US006809826B2

(12) United States Patent
Robertson

(10) Patent No.: US 6,809,826 B2
(45) Date of Patent: *Oct. 26, 2004

(54) LIQUID PHOTOMETER USING SURFACE TENSION TO CONTAIN SAMPLE

(76) Inventor: Charles William Robertson, P.O. Box 154, Rockland, DE (US) 19732

(*) Notice: Subject to any disclaimer, the term of this patent is extended or adjusted under 35 U.S.C. 154(b) by 327 days.

This patent is subject to a terminal disclaimer.

(21) Appl. No.: 10/078,717

(22) Filed: Feb. 19, 2002

(65) Prior Publication Data

US 2002/0140931 A1 Oct. 3, 2002

Related U.S. Application Data

(60) Provisional application No. 60/269,901, filed on Feb. 20, 2001.

(51) Int. Cl.[7] .............................................. G01N 21/01
(52) U.S. Cl. ....................... 356/440; 356/436; 356/246
(58) Field of Search ................................ 356/246, 436, 356/440

(56) References Cited

U.S. PATENT DOCUMENTS 4,286,881 A * 9/1981 Janzen ...................... 356/440

| 4,643,580 A | 2/1987 | Gross et al. |
| 4,910,402 A | 3/1990 | McMillan |
| 5,739,432 A | 4/1998 | Sinha |
| 5,926,262 A | 7/1999 | Jung et al. |
| 6,628,382 B2 | 9/2003 | Robertson |

FOREIGN PATENT DOCUMENTS

WO          WO 01/14855 A1     3/2001

OTHER PUBLICATIONS

World Precision Instruments Laboratory Equipment Catalog Sarasota, FL, US pp. 114–115 117–118.
Ocean Optics Cuvette Holders for 1–cm Cuvettes Dunedin, FL, US pp. 1–4.

* cited by examiner

*Primary Examiner*—Richard A. Rosenberger
(74) *Attorney, Agent, or Firm*—Edward J. Kaliski

(57) ABSTRACT

Method and apparatus of spectroscopy or the like on extremely small samples in which a drop is held between two opposing surfaces by surface tension and one surface is controllably toward and away from the other. To provide and transmit exciting energy through the drop for measurement, optical fibers go through a surface and finish flush with the surface. One of the surfaces can be swung clear of the other for easy cleaning between tests. Means for determining wetted surface are provided.

7 Claims, 22 Drawing Sheets

LIQUID PHOTOMETER USING SURFACE TENSION TO CONTAIN SAMPLE

FIELD OF INVENTION

The invention relates to the fields of photometry, spectrophotometry, fluorometry, spectrofluorometry and the like and their use in optically quantitating and or characterizing liquids and solutions.

BACKGROUND OF INVENTION

This invention relates to the field of spectrophotometers and related instruments. More particularly the invention relates to ultra low volume instruments working in the volume range of 2 microliters or less. Such devices are particularly useful in quantitation of biotechnology samples including nucleic acids or proteins where it is desirable to keep sample loss and/or cross-contamination to a minimum.

Robertson, in International Publication Number WO 01/14855, discloses method and apparatus for liquid photometry on extremely small samples. Robertson is the inventor of the instant invention which is an improvement thereon The disclosure, of the publication is incorporated herein by reference. A U.S. nation stage application was entered into for that reference and has issued as U.S. Pat. No. 6,628,382. The prior art to WO 01/14855 A1 contains examples of attempts to supply low volume instruments. World Precision Instruments of Sarasota, Fla. offers parts from which an instrument handling less than 20 microliters can be built for around $3000. This uses a fiber optic dipping probe with a tip diameter of 1.5 mm (Dip Tip®), their miniature fiber optic spectrometer and F-O-Lite H light source. With a deuterium lights source (D2Lux) a UV spectrophotometer can be constructed.

U.S. Pat. No. 4,643,580 to Gross et al. discloses a photometer head in which there is a housing for receiving and supporting small test volumes. A fiber optic transmitter and receiver are spaced within the housing so that a drop can be suspended between the two ends.

McMillan, in U.S. Pat. No. 4,910,402, discloses apparatus in which a syringe drops liquid into the gap between two fixed fibers and an IR pulse from a LED laser is fed through the droplet. The output signal is analyzed as a function of the interaction of the radiation with the liquid of the drop.

Ocean Optics, of Dunedin, Fla. 34698 supplies a SpectroPipetter for microliter-volume samples using a sample volume of about 2 microliters. The optics not only carry light to and from the samples but act as a plunger to load the sample. The tip of the pipette includes the sample cell.

Liquids, mixtures, solutions and reacting mixtures are often characterized using optical techniques such as photometry, spectrophotometry, fluorometry, or spectrofluorometry. In order to characterize samples of these liquids, the liquid is usually contained in a vessel referred to as a cell or cuvette two or more of whose sides are of optical quality and permit the passage of those wavelengths needed to characterize the liquid contained therein. When dealing with very small sample volumes of say from 1 to 2 microliters, it is difficult to create cells or cuvettes small enough to to be filled and permit the industry standard 1 cm optical path to be used. It is also difficult and/or time consuming to clean these cells or cuvettes for use with another sample. In the case of photometry or spectrophotometry, the value most commonly sought is the sample absorbance A defined by $$A = -\log T$$

Where T is the transmittance, or $$A = \log(l/l_0)$$

where $l_0$ is the level of light transmitted through a blank sample (one containing all components except the one being measured or one whose absorbance is known to be negligible and with optical properties identical to those of the sample being measured), and l the level of light transmitted through the sample being measured. Most commonly the absorbance value is measured in a cell or cuvette with a 1 cm path length. However, Lambert's Law states that for a collimated (all rays approximately parallel) beam of light passing through a homogeneous solution of uniform concentration the absorbance is proportional to the path length through the solution. For two path lengths X and Y, (Absorbance $x$)/(Absorbance $y$)=(Pathlength $x$)/(Pathlength $y$)

Thus it is reasonable that absorbance can be measured with path lengths other than 1 cm and corrected for path length to the equivalent value for a 1 cm path which can be more easily compared to data from other spectrophotometers. The sample path lengths in the range of 0.2 to 2 mm used in this Invention can be used to generate absorbance values that can be easily corrected to the 1 cm path equivalent.

Although liquids confined by surface tension and an optical surface are well known, e.g. raindrops on the window, establishing a collimated optical light path of known length through such confined liquids has been perceived as difficult. The recent advent of small spectrometers designed to be used with fiber optics has made it possible to consider spectrophotometric geometries not readily possible before.

This invention uses the surface tension of a microliter or submicroliter sample of liquid to provide sufficient means to confine it within the analysis region of an optical analysis instrument and to carry out the requisite measurement.

STATEMENT OF INVENTION

The invention is an optical instrument for photometric, spectrophotometric, fluorometric or spectrofluorometric analysis of liquids contained between two substantially parallel surfaces on anvils spaced apart a known distance, wherein the sample liquid is confined by the surfaces and the surface tension of the liquid. At least two optical fibers penetrate these surfaces. One fiber is the source and the other the receiver. Ordinarily each of the surfaces contains an optical fiber. These fibers are mounted coaxially with and perpendicular to the parallel confining surfaces. The shape and nature of the surfaces serve to confine the liquid so as to center the confined droplet in the optical path of the optical fibers imbedded in the surfaces. An apparatus supporting the surfaces permits the surfaces to be controllably separated tho allow loading of the sample and cleaning of the surfaces after sample analysis as well as to pull a column of controlled length in the sample to set the optical path length during measurement. The surfaces can be separated enough that both surfaces can have a nanodrop applied so that mixing or reacting can be carried out and observed. The surfaces can be moved into a close position for sample compression as a wetting aid or, in some instances, as an alternate loading position.

For some applications, the optical fibers can be replaced by miniature sources like light emitting diodes (LEDs) and detectors or detectors with optical filters. The LEDs with their characteristically small emitting area would replace the source fiber and small solid state detectors with associated filters like those used in color charge coupled devices (CCDs) for imaging would replace the receiving fiber and spectrometer.

DESCRIPTION OF THE INVENTION

Figure 1:
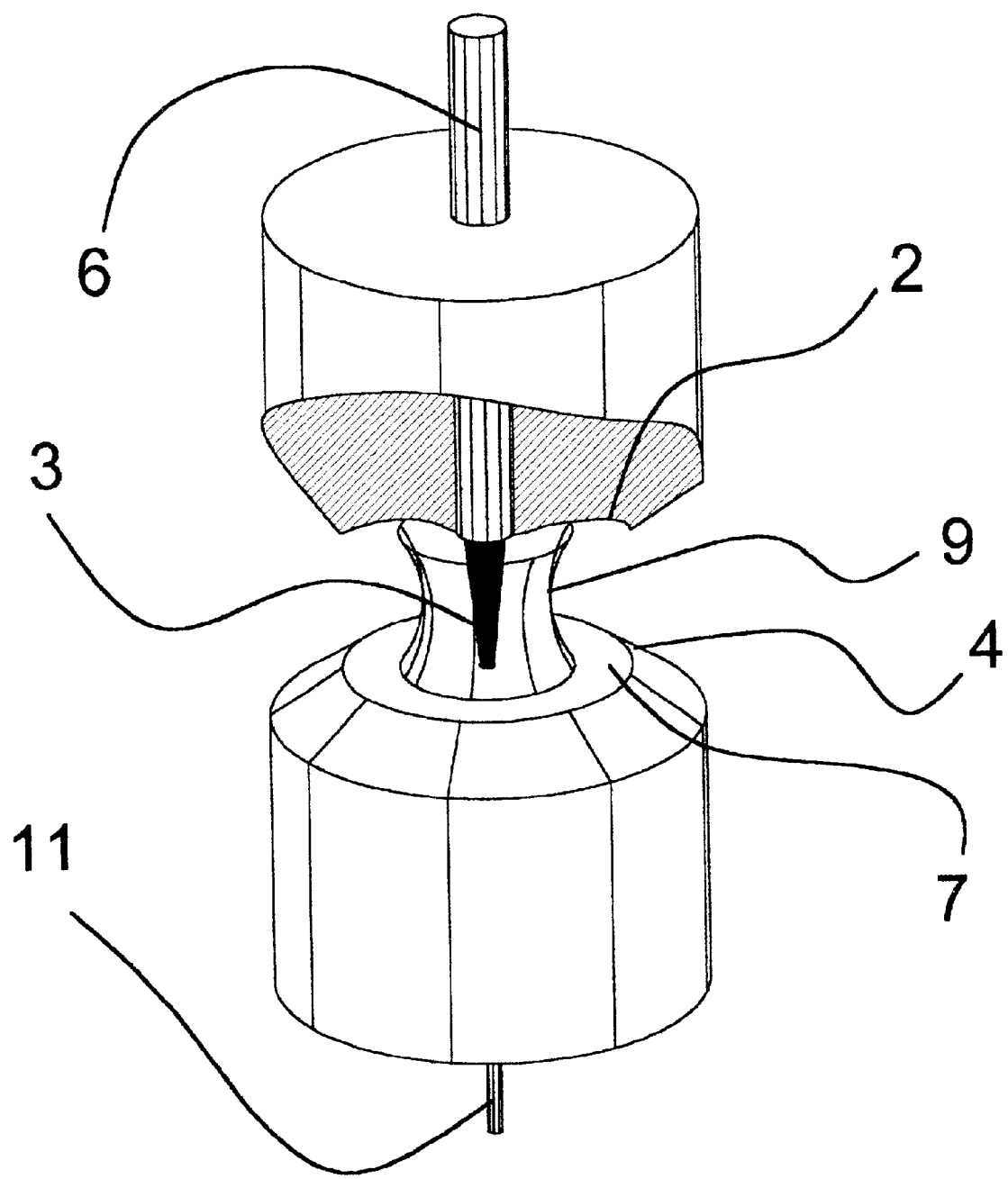
FIG. 1 is a view of a cutaway sections of the optical path of the invention.

The liquid sample shown in FIG. 1 is contained by its surface tension between surfaces 2 and 7 also shown in FIG. 1. Light 3 from the system source (such as 74 in FIG. 4a) coming through the fiber 11 contained in surface 7 radiates upward 3 through the liquid sample 9 and is collected by the larger fiber or light pipe 6 in the upper surface 2 and sent on to the analysis photometer or spectrometer (such as 70 in FIG. 4a) for absorbance measurements.

Figure 2:
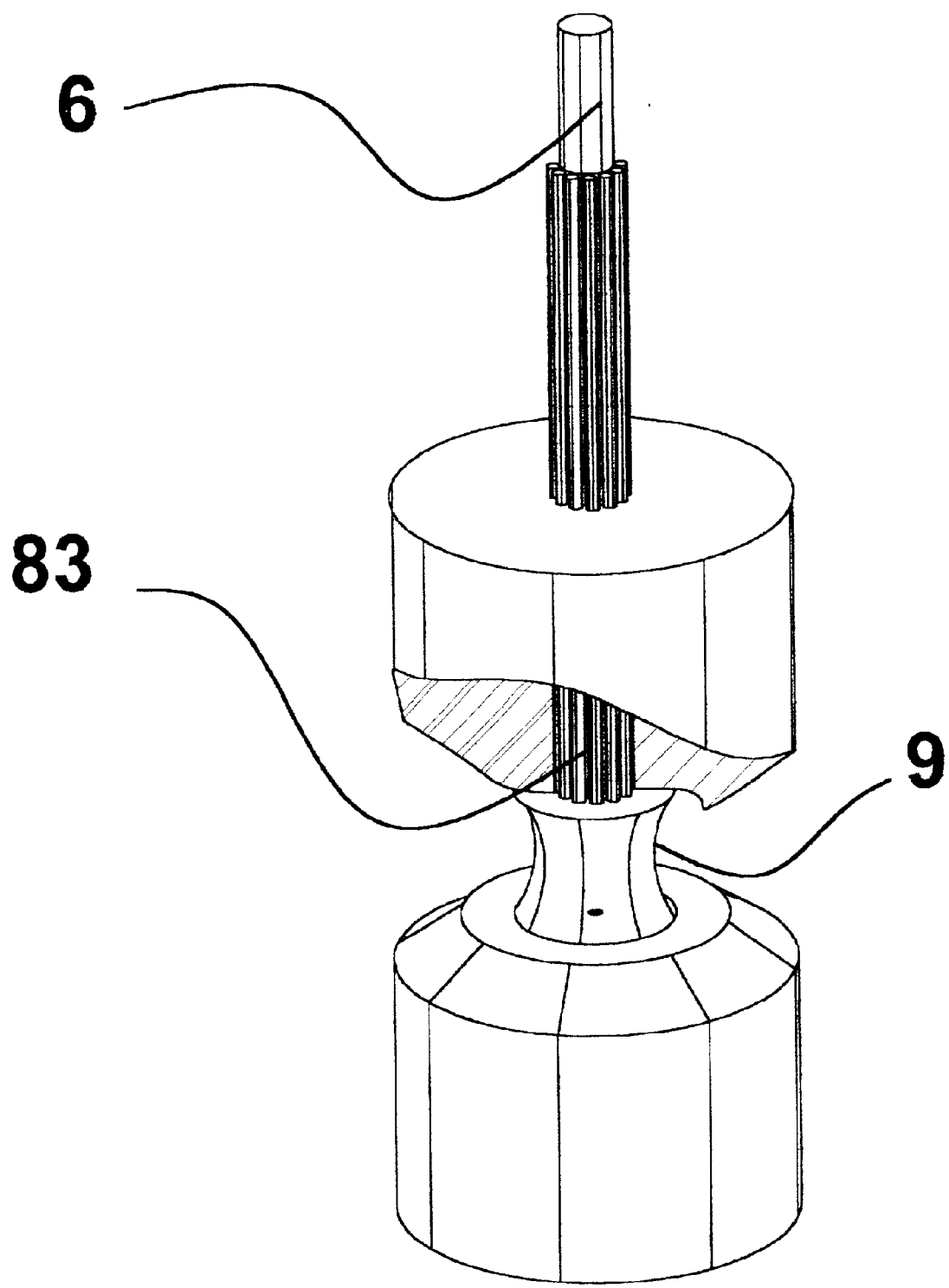
FIG. 2 is a drawing of a cutaway section of the optical path of the invention with additional fluorometric source optical fibers shown.

Measurements of the level of fluorescence of samples can be made by adding an excitation filter to the light source (not shown) and an emission filter to the detector (also not shown) to specifically reject all light from the excitation source at the detector. The level of fluorescence will, thus, be directly dependent on the length of the optical path between the anvils. The excitation can also be brought to the sample 9 through fibers 83 surrounding the collection fiber 6 as is shown in FIG. 2. This reduces the need for a high level of excitation wavelength rejection on the part of the spectrometer or other detector collecting the light from the sample through collection fiber 6.

Figure 3A:
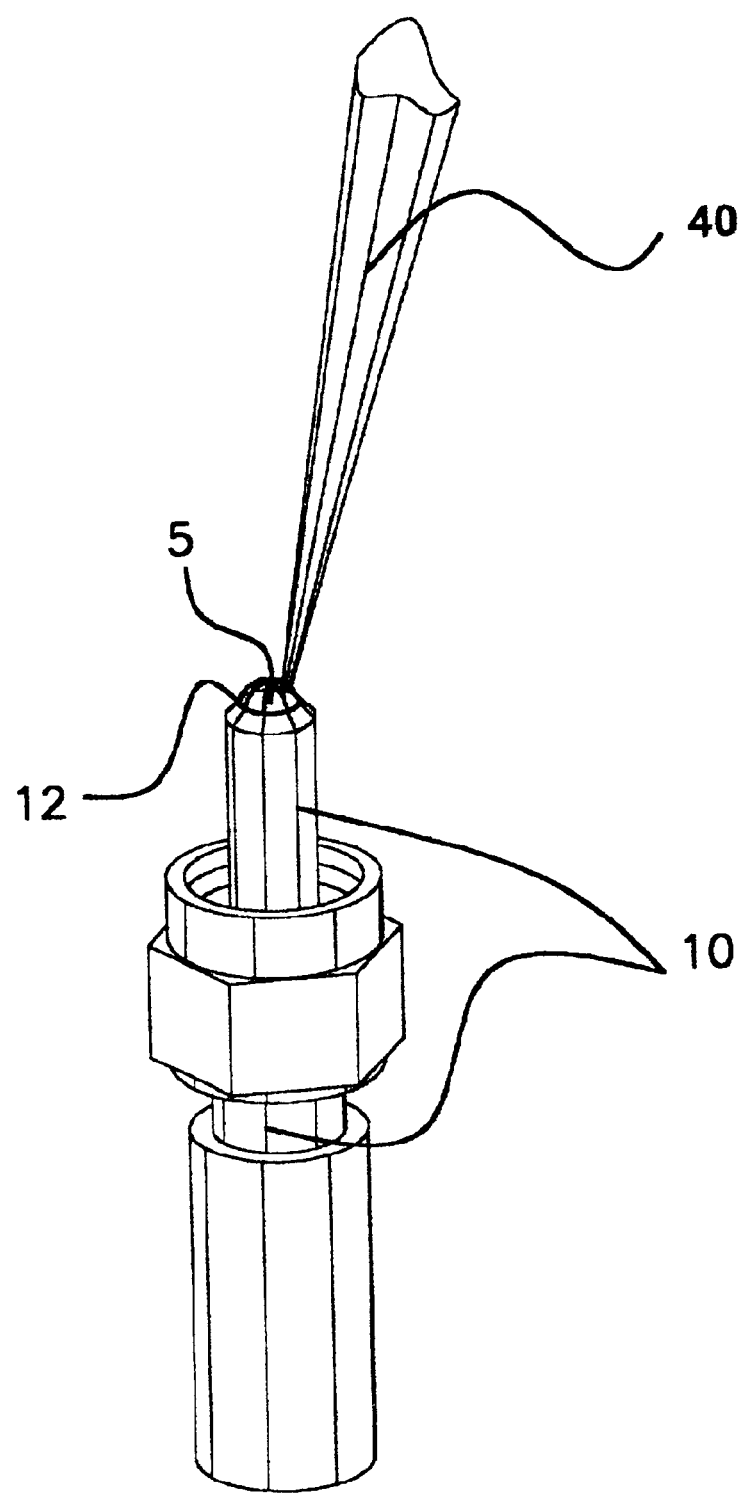
FIG. 3a is a perspective view of a process by which the sample is loaded into the optical path of the invention.
Figure 12A:
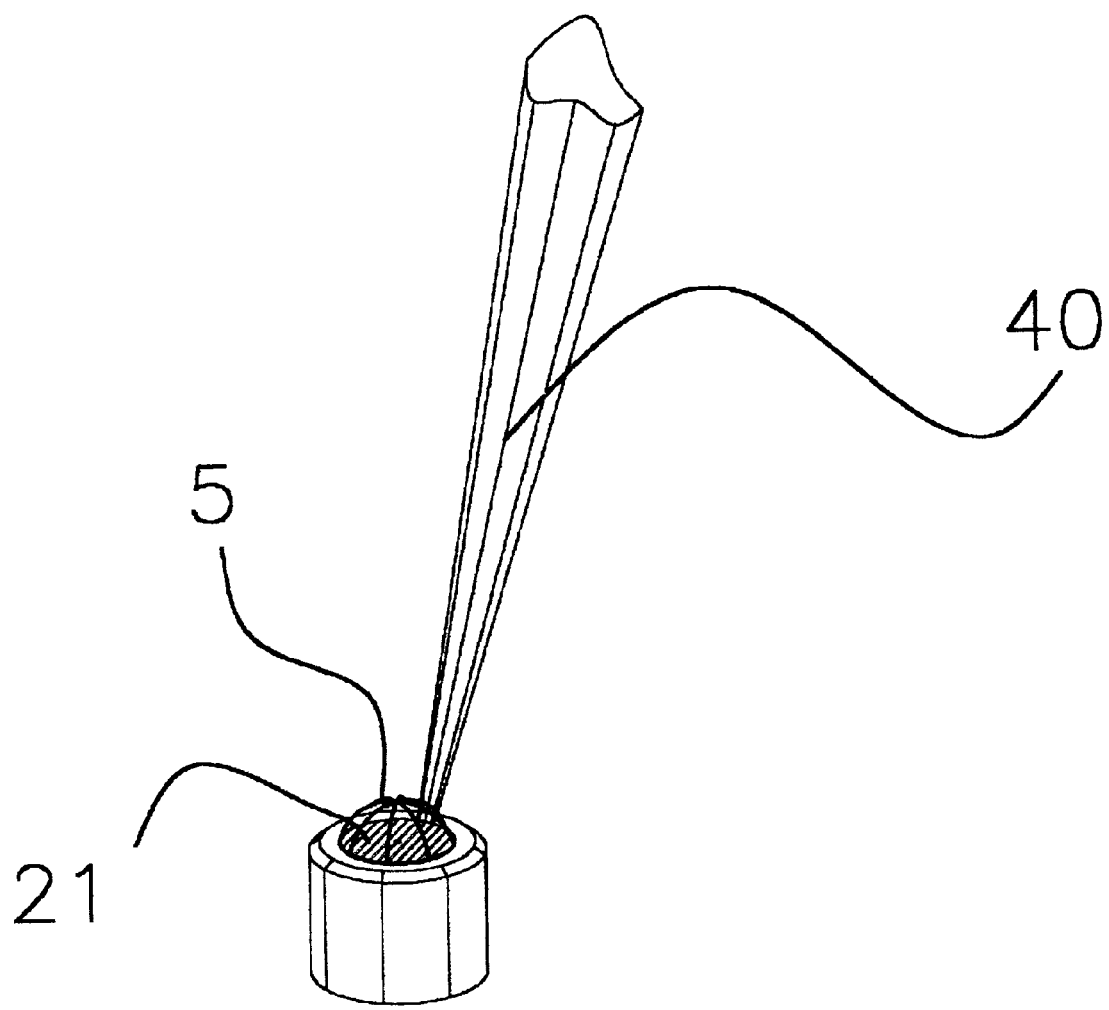
FIG. 12a is a perspective view of the sample being loaded into the apparatus with the area wetted by the sample controlled by a change in surface wetting characteristics using an attractive surface internal area.
Figure 12B:
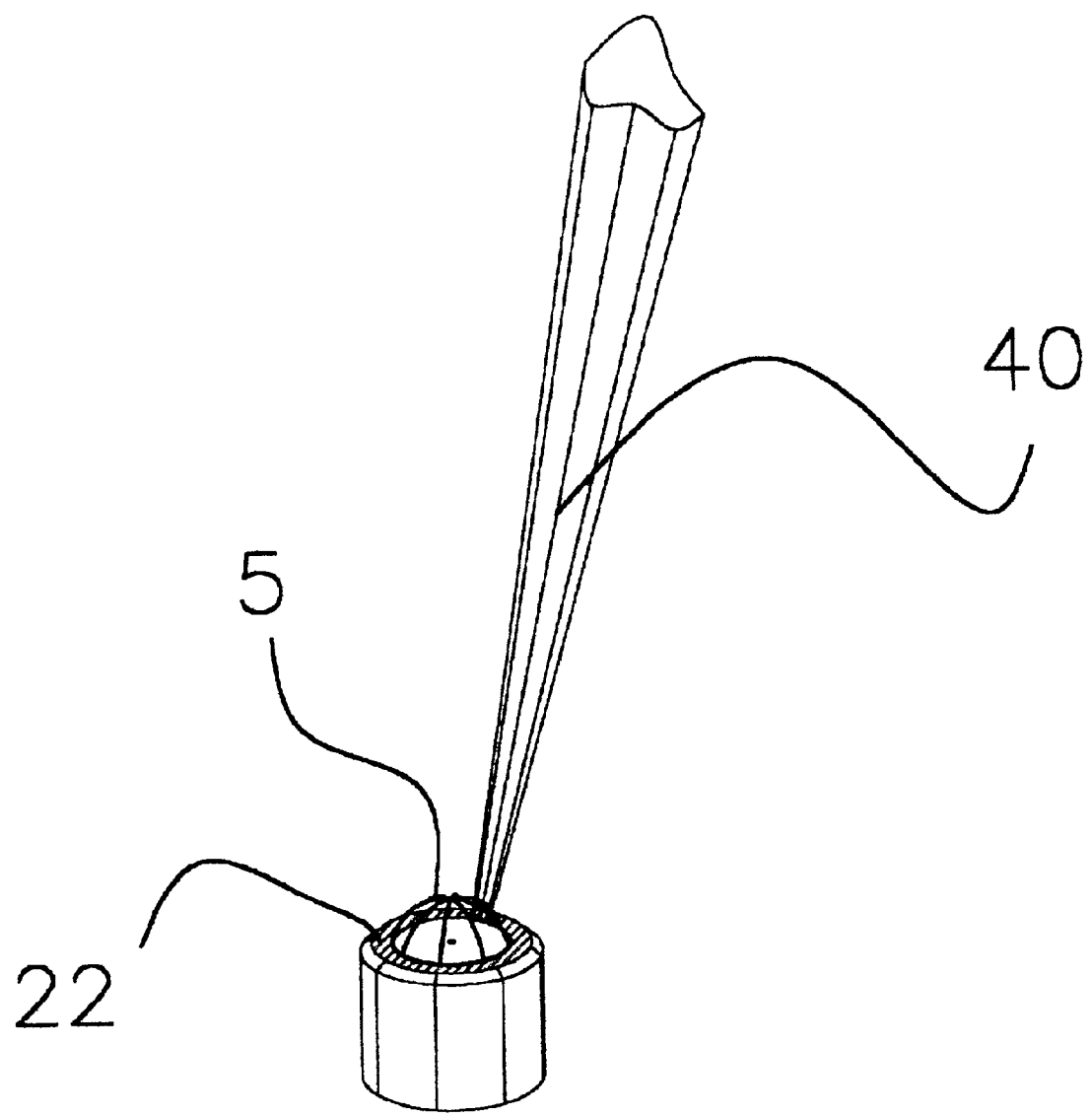
FIG. 12b is a perspective view of the sample being loaded into the apparatus with the area wetted by the sample controlled by a change in surface wetting characteristics using a repulsive surface outside area.

Samples are loaded onto one of two roughly identical anvil surfaces, usually the lower anvil surface, with a pipetting means 40, (FIG. 3a) such as a 2 microliter Pipetteman® from the Ranin® Corporation of Woburn, Mass., part of the tip of which is shown in 40. The droplet 5 when emptied from the pipette 40, if of sufficient volume, will spread to cover the lower anvil surface 7, FIG. 1, which is typically the end of an industry standard SMA fiber optic connector 10, FIG. 3a (found as connectors on the ends of optical patch cords like p/n P-400-2-UV-VIS from Ocean Optics inc. of Dunedin, Fla.) until it encounters the sharp edge shown as 4, FIG. 1. For most SMA connectors the approximate 2 mm end diameter can be effectively covered with 2 microliters of Sweater or a water-based solutions. Alternatively the spread of the sample can be limited by a change in the surface tension characteristic. This is shown in FIGS. 12a and 12b. Here a polymer surface of a material like Teflon™ can be used to limit the spread by the edge of the polymer film to an area bounded either on the inside, as seen at 21, FIG. 12a, or outside, as seen at 22 in FIG. 12b.

Figure 3B:
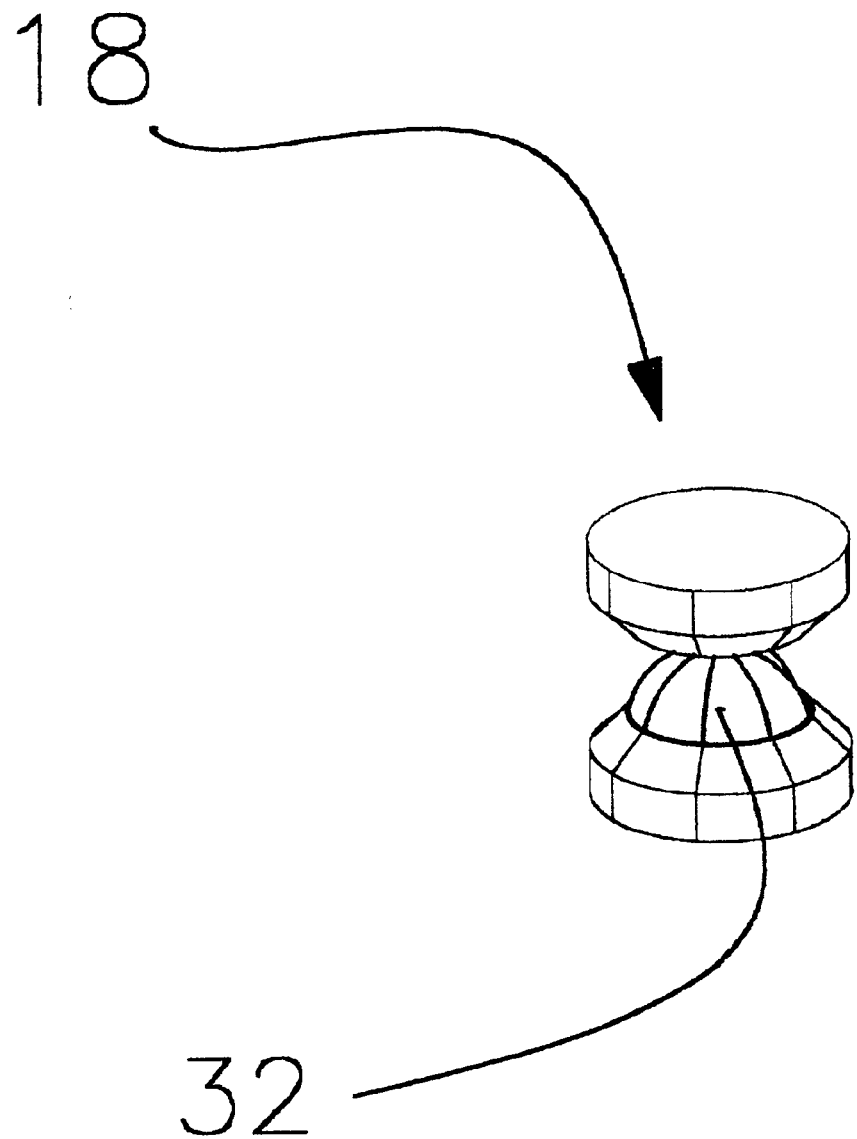
FIG. 3b shows the sample between the two anvils in the measurement position before the second surface is wetted.
Figure 3C:
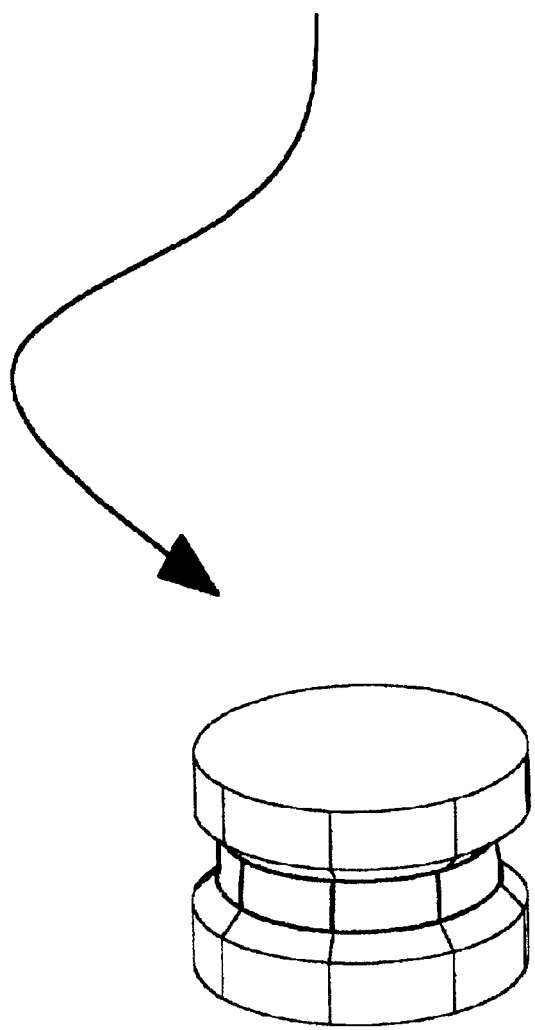
FIG. 3c shows the sample compressed between the two anvils in the short path or sample compression position.
Figure 3D:
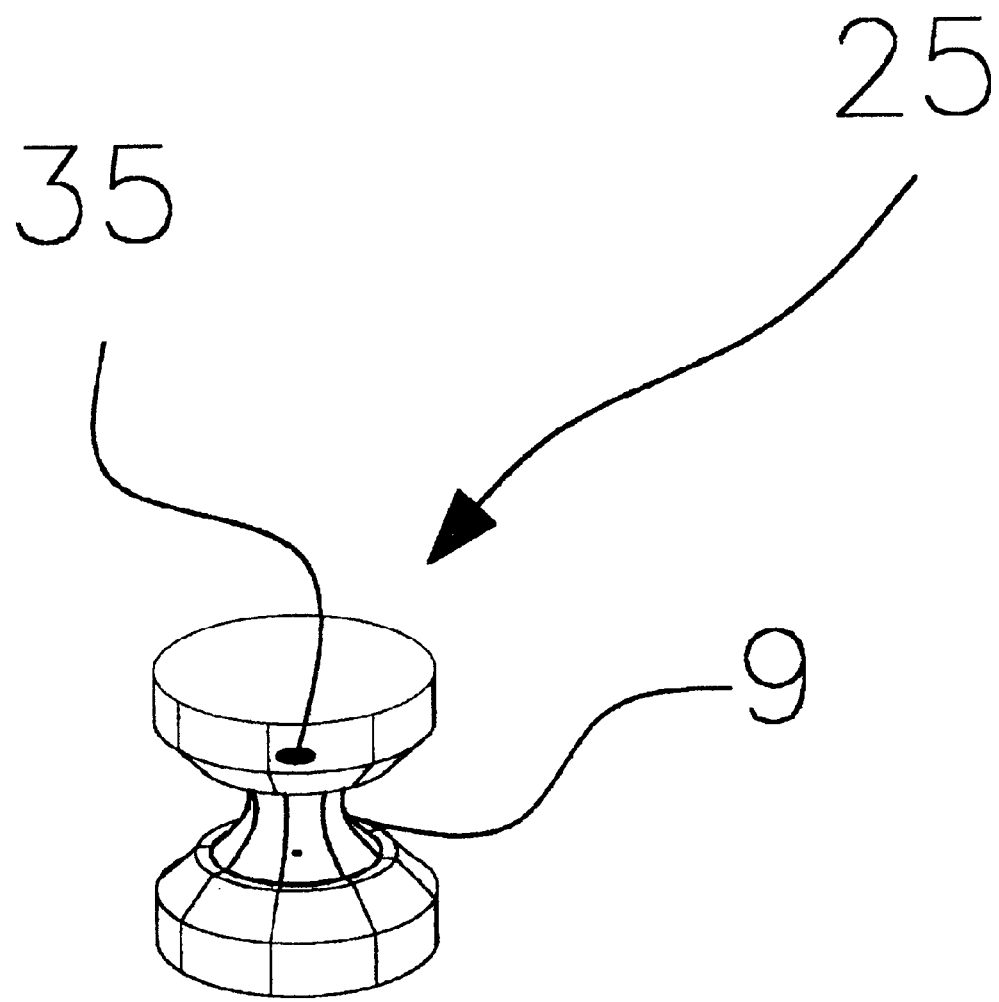
FIG. 3d shows the sample column drawn by opening the anvils from the sample compression position to the sample measurement position

The second anvil surface 2 is brought into the measurement position 18, FIG. 3b, and then into dose proximity 20 to the first anvil surface 7, FIG. 3c, making contact with the deposited droplet 5 wetting the entire confining surface before returning to the sample measurement position and drawing up the sample measurement column 9, FIG. 3d, shown at 25.

Figure 4A:
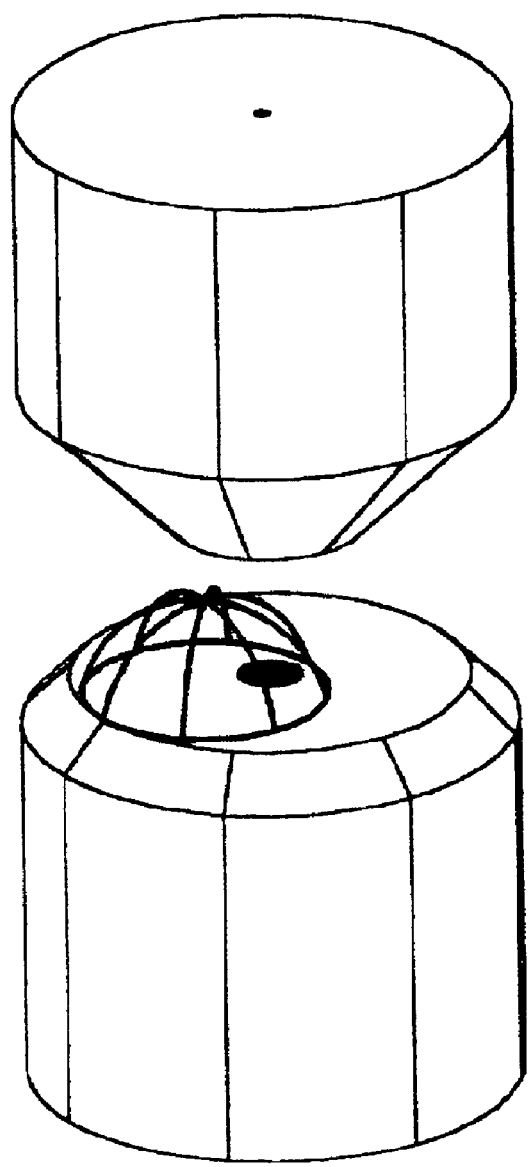
FIG. 4a shows a small, typically 1 microliter or less, sample loaded on top the lower anvil with the apparatus closed.
Figure 4B:
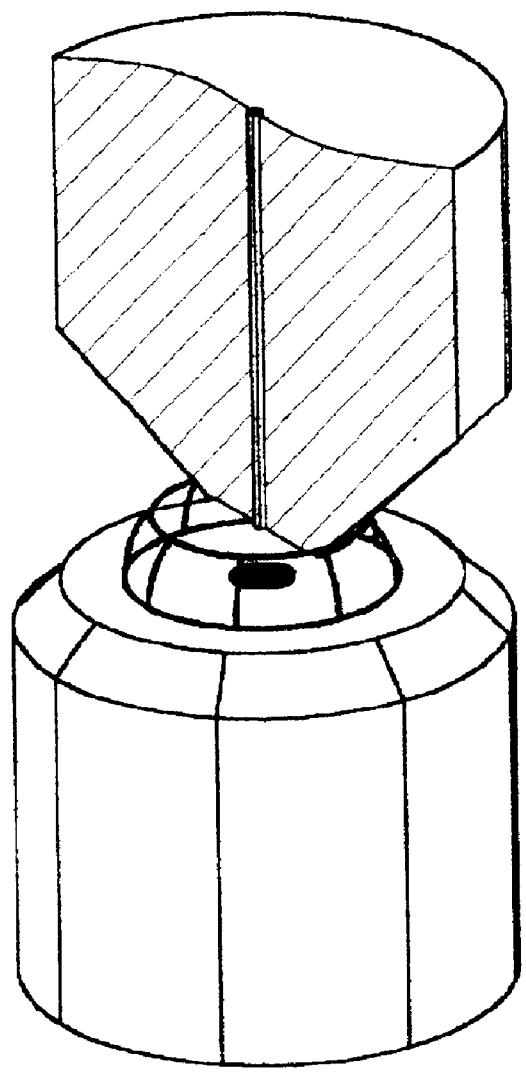
FIG. 4b shows the small sample pulled into the space between the anvils in the compression position by capillary action.
Figure 4C:
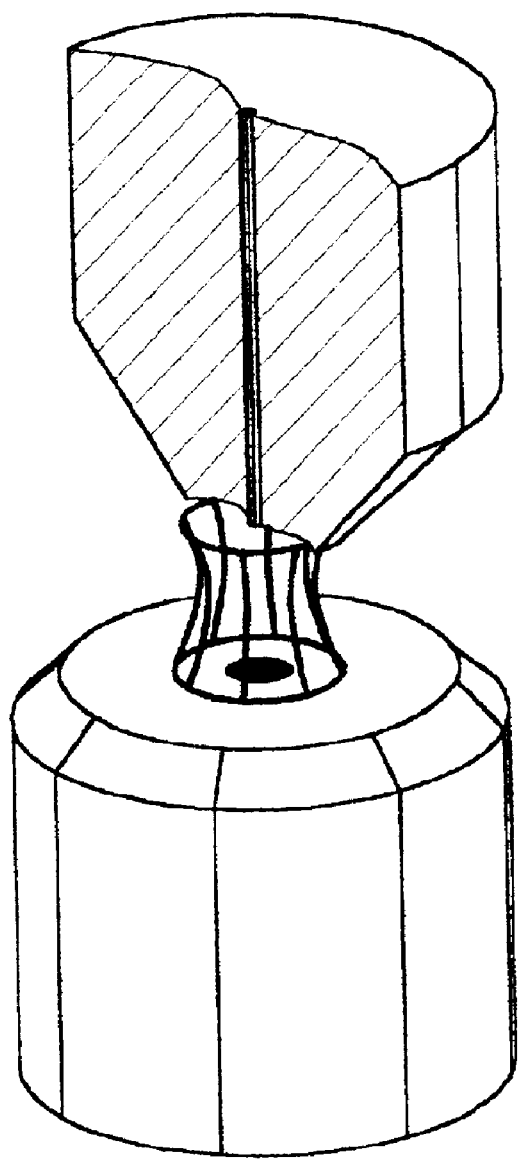
FIG. 4c shows the small sample pulled into a measurement column between the smaller upper anvil and the larger lower anvil.

Alternatively the anvils can be of unequal size as shown in FIGS. 4a, 4b, and 4c. Here the lower, larger anvil 8 presents a larger loading target. The sample will stay within the edge 4 defining the boundary of the anvil. When the smaller, upper anvil 13 is brought into sample compression position as shown in FIG. 4b, the sample will be pulled into the gap between anvils by capillary action. The smaller second anvil diameter serves to center small samples in the measurement path 3, FIG. 1, when the measurement column 9, FIG. 4c, is pulled. The larger diameter 15 is shown in the lower anvil with the smaller fiber 17 in the smaller anvil.

By applying blank samples, samples missing the component being analyzed, the difference in transmitted light intensity can be used to characterize the sample according to $$A = -\log(I/I_0)$$

where $I_0$ is intensity of transmitted light through the blank sample, a sample with the component being analyzed absent, and $I$ is the intensity of light transmitted through the sample and A is the absorbance value which can be related to the concentration of the component being analyzed by Beer's law which states that for solutions 1 and 2 that $$\frac{(\text{Absorbance 1})}{(\text{Absorbance 2})} = \frac{(\text{Concentration 1})}{(\text{Concentration 2})}$$

Thus, when compared with a blank sample, the concentration of the component of interest being analyzed can be directly determined from the absorbance A.

Figure 11:
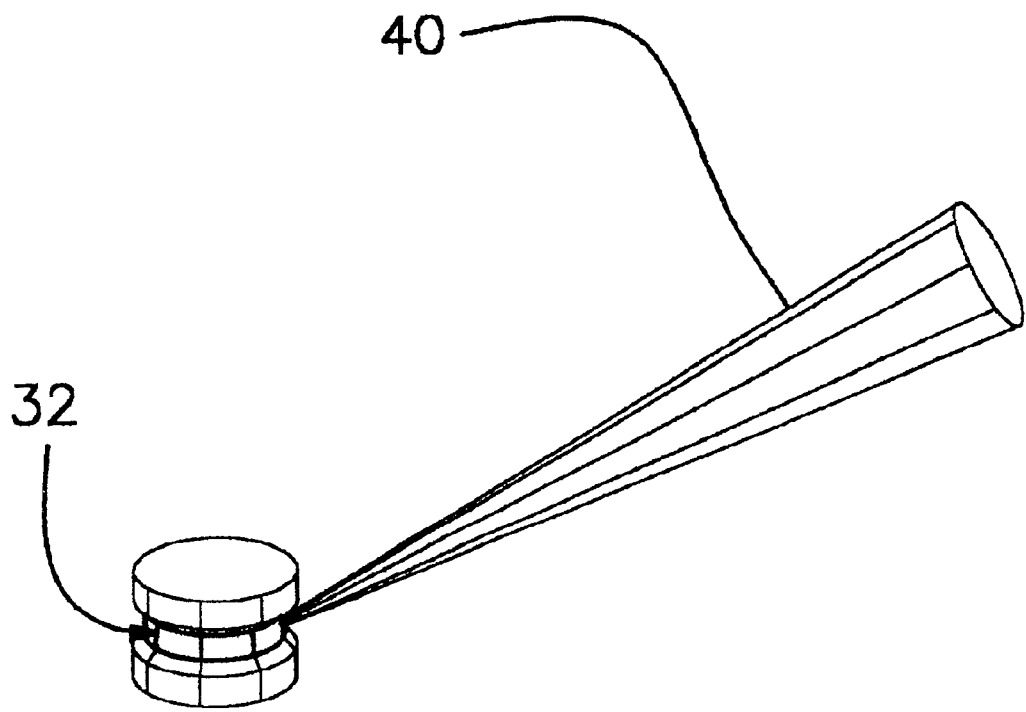
FIG. 11 is a perspective view of the sample being loaded into the apparatus with the anvils in a close spaced position like the compression position.

Alternatively, the sample 32 can be loaded as shown in FIG. 11 where the pipette tip 40 applies the sample to the space between the anvils while they are ion close proximity as in the compression position shown in FIG. 3c. This is similar to the sample loading procedure taught by Gross et al. The measurement column can then be drawn to an appropriate length and the photrometric or spectrophotometric measurement made.

Figure 5A:
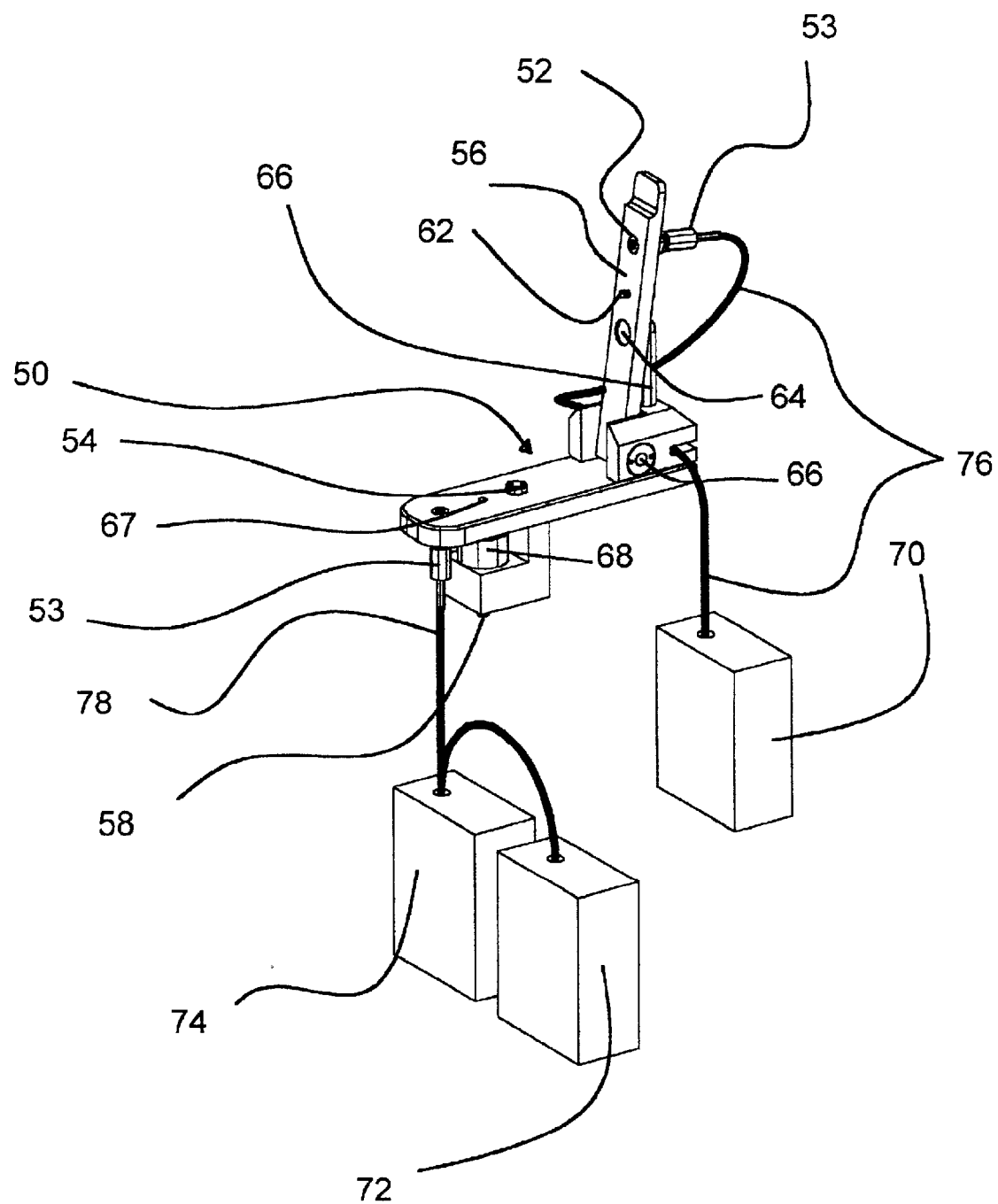
FIG. 5a is a perspective view of apparatus of the invention in its open position with the source and spectrometers.
Figure 5B:
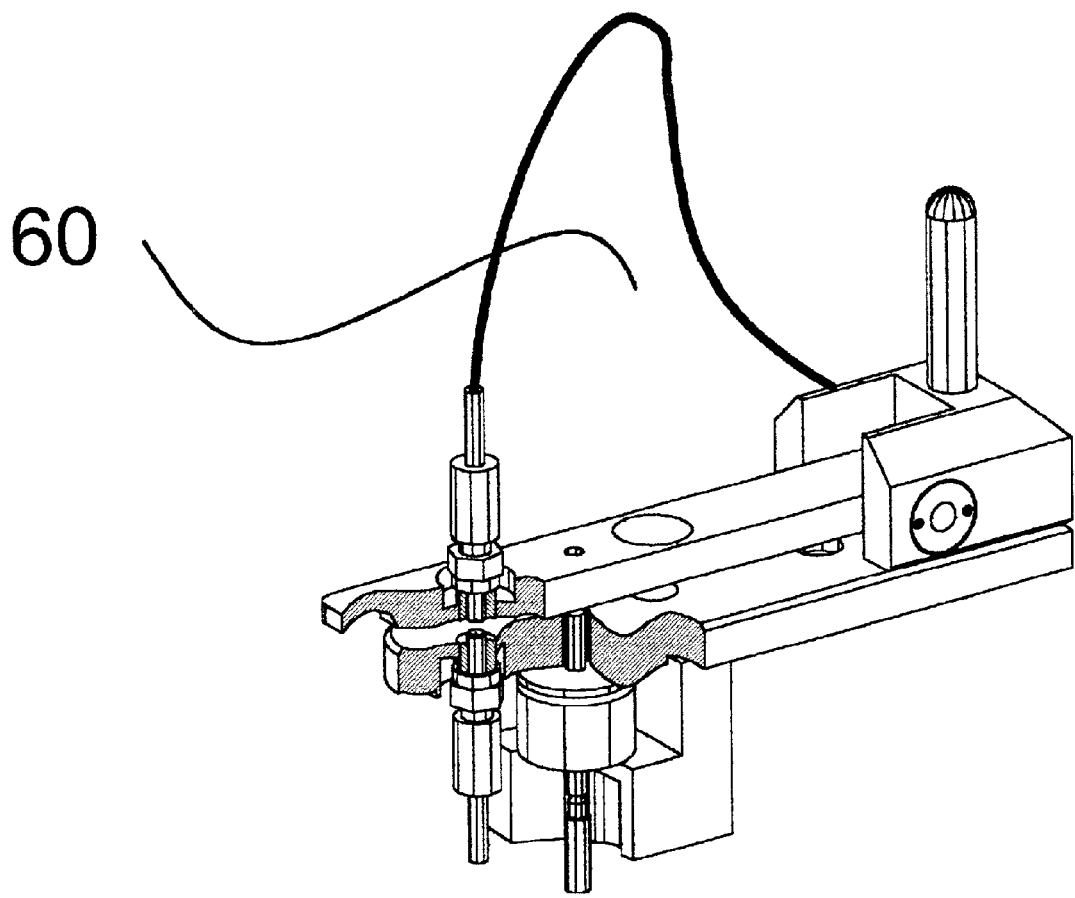
FIG. 5b shows a cutaway view of the apparatus in its closed position as it would be for sample compression or analysis.

The SMA optical fiber connectors can be held in place by apparatus shown in FIGS. 5a and 5b. The light from the system source 74 (Ocean Optics inc. p/n DT-1000, a combined deuterium arc and quartz halogen incandescent lamp, alternatively a xenon flashlamp can be used) is coupled through a bifurcated optical fiber assembly 78 (Ocean Optics inc. p/n BIF-100-2-UV-VIS) to the apparatus 50 with the second fiber of the bifurcated assembly 78 going to reference slave spectrometer 72 (Ocean Optics p/n SD2000). The SMA connectors 53 are mounted to the apparatus by means of threaded couplers 52 (World Precision Instruments p/n 13370) which are threaded into the apparatus. The swing arm 56 carrying the upper optical fiber 53 can be lowered to align the source with the detection fiber as is shown in 60, FIG. 4b. The swing arm spacing is controlled by pin 62 resting on the plunger 67 of solenoid 68 (Lucas Ledex of Vandalia, Ohio p/n 174534-033) shown mounted below the apparatus. The other end of the solenoid plunger 67 rests on spring plunger 58 (Manhattan Supply of Plainview, N.Y. p/n 82412032). The sample can be compressed as is shown in 20, FIG. 3c, by manually pushing on the swing arm 56 so as to push the solenoid plunger to the limit of its travel or by actuating the solenoid electrically and pulling the plunger to its stop. The swing arm is held in both its up and its down, position by magnet 64 (Edmund Scientific of Barrington, N.J. p/n J35-105) attracted to either post 65 or allen head cap screw 54. With the swing arm in its raised position, the sample detection surfaces may be cleaned by wiping the sample from both the lower and upper SMA connector ends before reloading.

Figure 7A:
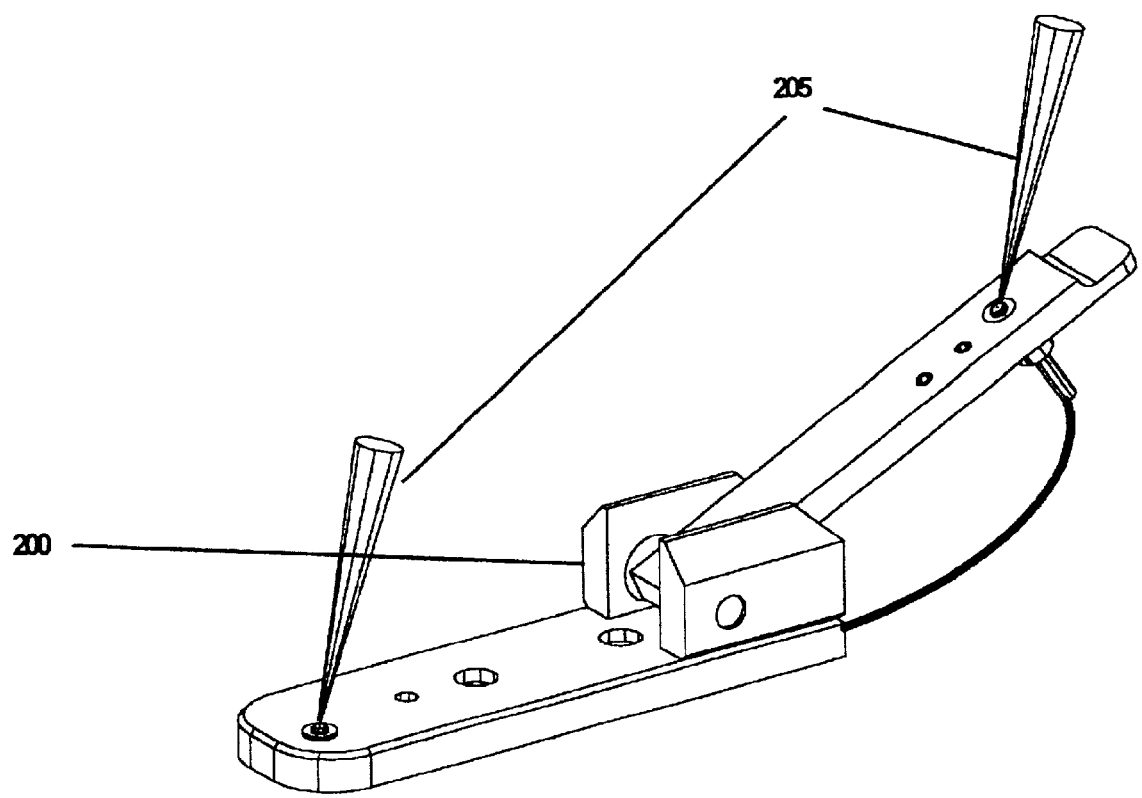
FIG. 7 is a perspective view of the open instrument showing two pipetter tips loading two parts of a mixture each on either side of the measurement apparatus.
Figure 7B:
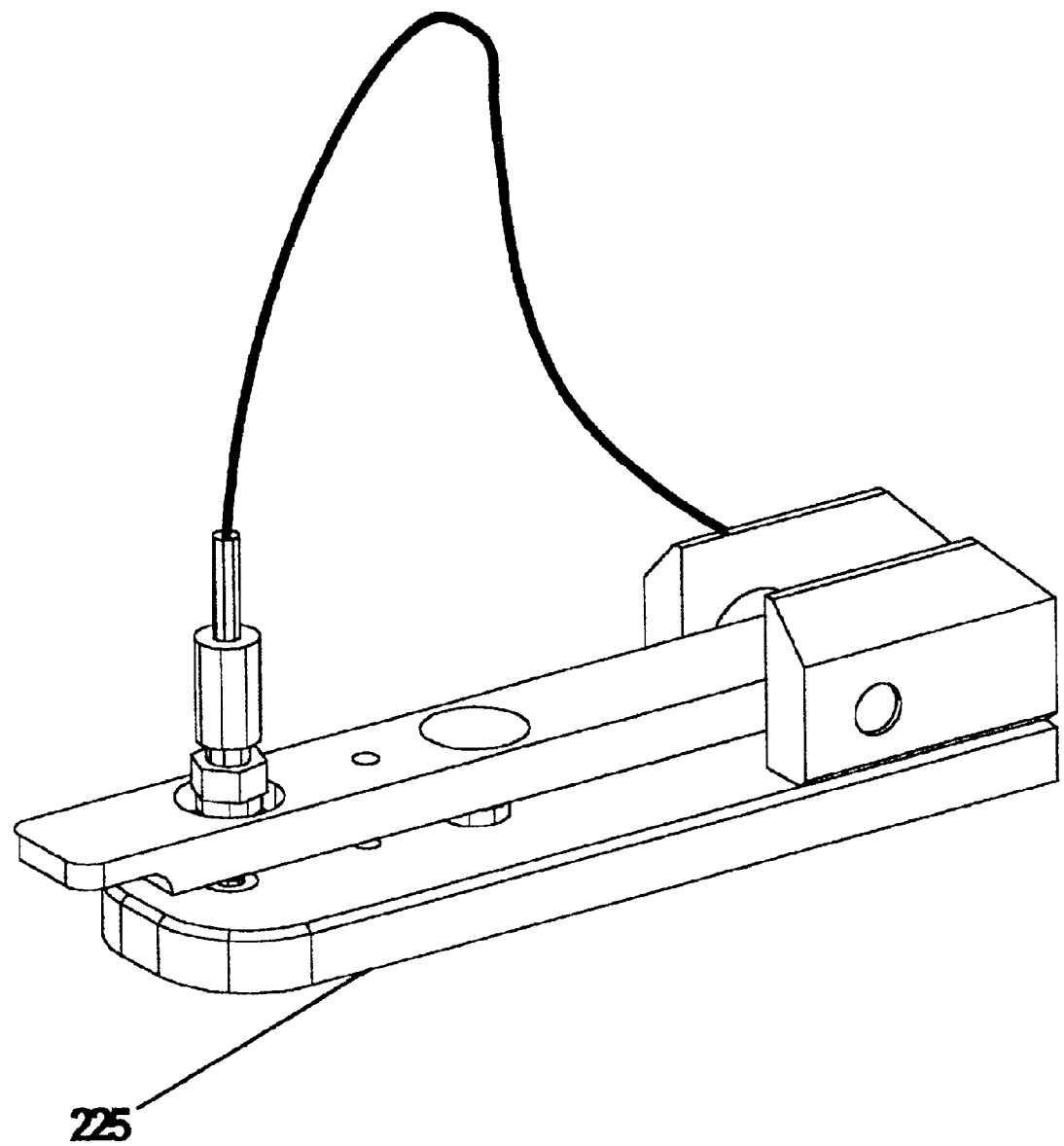

Light transmitted through the sample is collected by the upper fiber and coupled to the detection master spectrometer 70 (Ocean Optics p/n SD2000). The fiber is confined to minimize flexure of the fiber which would cause unnecessary variability in its transmission and thus unnecessary variation in measured absorbances. The swing arm is precision pivoted on a shaft turning in two preloaded ball bearings 66. Note that the instrument is opened by turning the swing arm 50 through an arc sufficient to permit loading and cleaning of the anvil surfaces. See FIG. 5a. Preferably it is opened at least 90 degrees as seen in FIG. 5a and more preferably the arc approaches 160 degrees as seen in FIG. 7.

In order to accomplish illumination of the sample for fluorescence as shown in FIG. 2, the upper fiber assembly is made so as to surround the collection fiber 6 with illumination fibers 83. These would be bundled and illuminated with the source wavelength compatible for use with the sample.

Figure 6A:
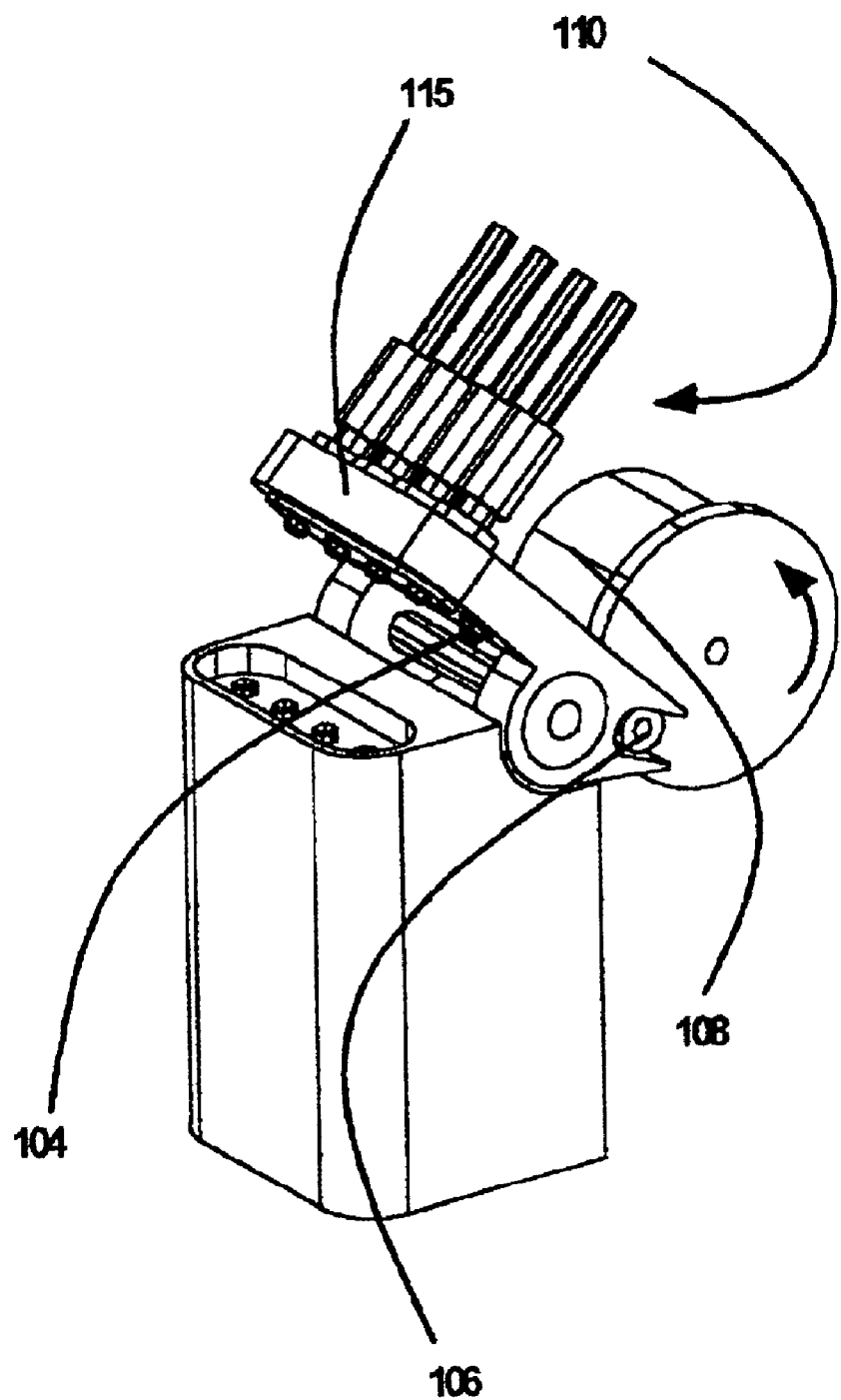
FIGS. 6a and 6b show a system with four spectrophotometer systems operating simultaneously for use on robotic platforms in both loading, 6a, and measuring, 6b, configurations respectively.
Figure 6B:
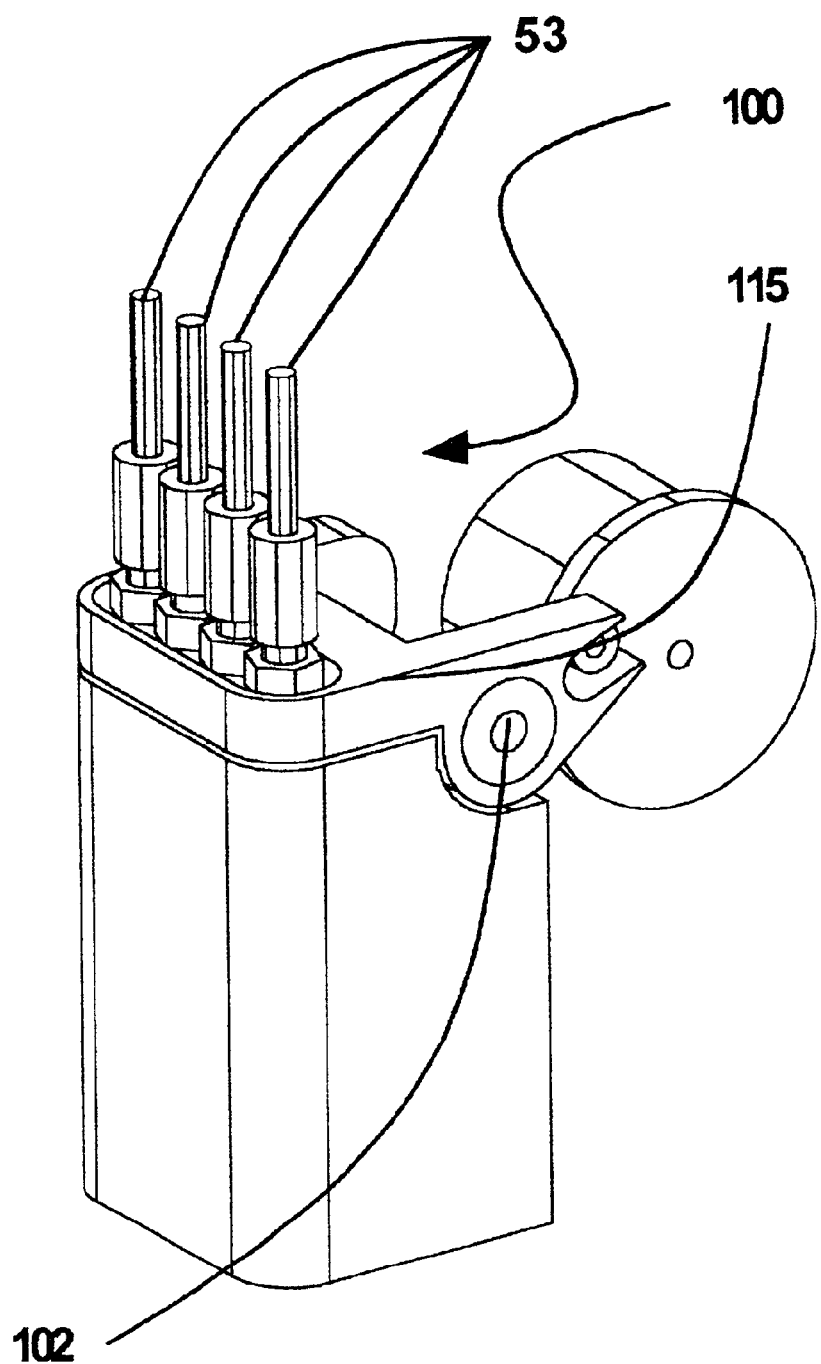

As seen in FIGS. 6a and 6b, two or more of the photometeric devices can be grouped in unitary form to measure multiple samples simultaneously. Such a multiple parallel photometer system can be employed with a multi-pipette robot system such as the MultiPROBE II made by Packard Instrument Company of Meriden, Conn. In FIG. 6, the four signal fibers 53 (which correspond to fiber 6 of FIG. 1) each feed a fiber optic spectrometer and the spectra are taken simultaneously. The four source fibers, not shown, are illuminated from a single source which may be referenced with a single reference spectrometer as with the single channel system. In FIG. 6b the apparatus is shown closed 100 and, in FIG. 6a, open for loading 110. Opening and closing are controlled by a rotary actuator 108 such as p/n 195191-031 made by Lucas Ledex of Vandalia, Ohio and cam 106. Spring plunger 104 such as p/n 3408A35 sold by McMaster-Carr of New Brunswick, N.J. controls the position and provides the spring force against which the compression over-travel is accomplished for initial wetting of the upper anvil surface by the sample.

Samples for photometric analysis can also be loaded into the sample handling apparatus in two parts, one on each of the opposing surfaces. This is especially useful where the sample of interest is a two part reacting mixture where the one or more of the beginning absorbance, the ending absorbance, and the rate of reaction are of interest and can be measured photometrically of fluorometrically. Samples of this sort can be loaded into the open spectrophotometer as shown in FIG. 7, where two pipetter tips 205 are shown loading the two parts of the mixture, each on either side of the measurement apparatus 200. When closed as shown in FIG. 5b, measurement can be made from onset of any reaction. The exact time of sample mixing or the initiation of a reaction can be determined from photometric or fluorometric measurement through the apparatus optical fibers.

Figure 8A:
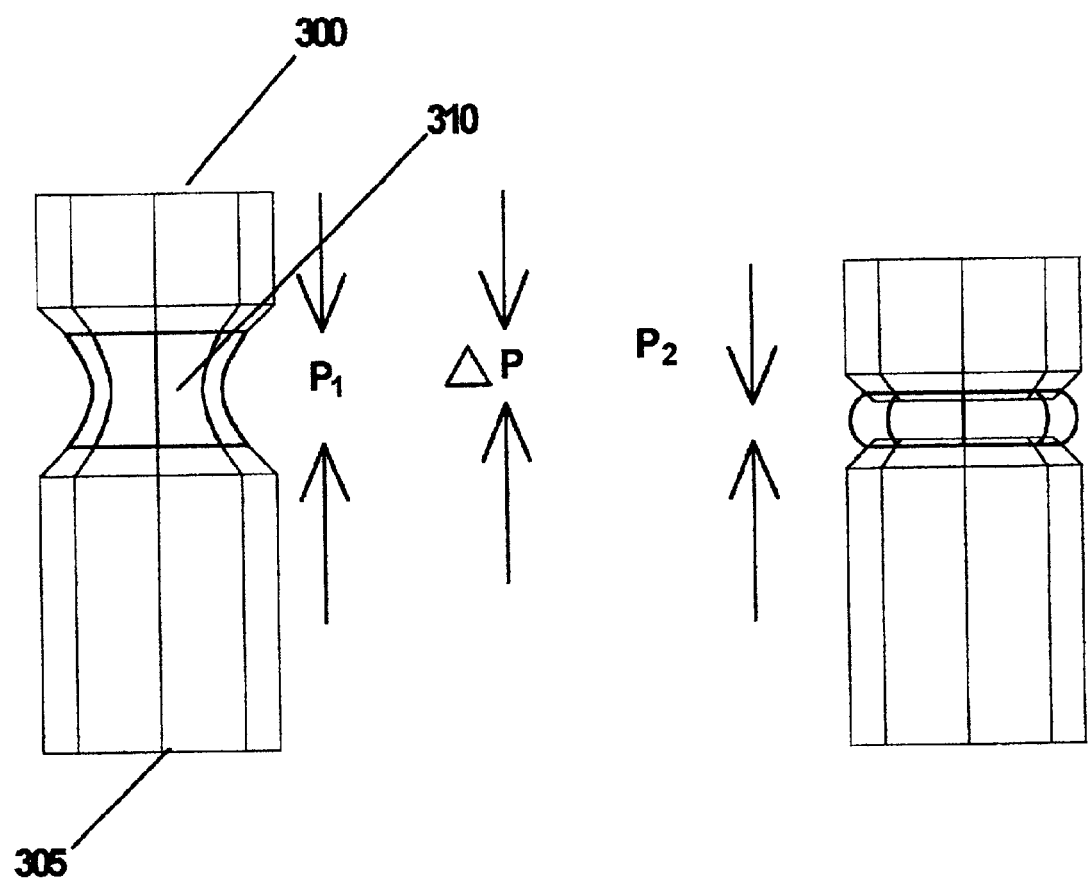
FIG. 8 shows perspective views of two path lengths provided by the apparatus of the invention so that a differential absorbance path is established.
Figure 8B:
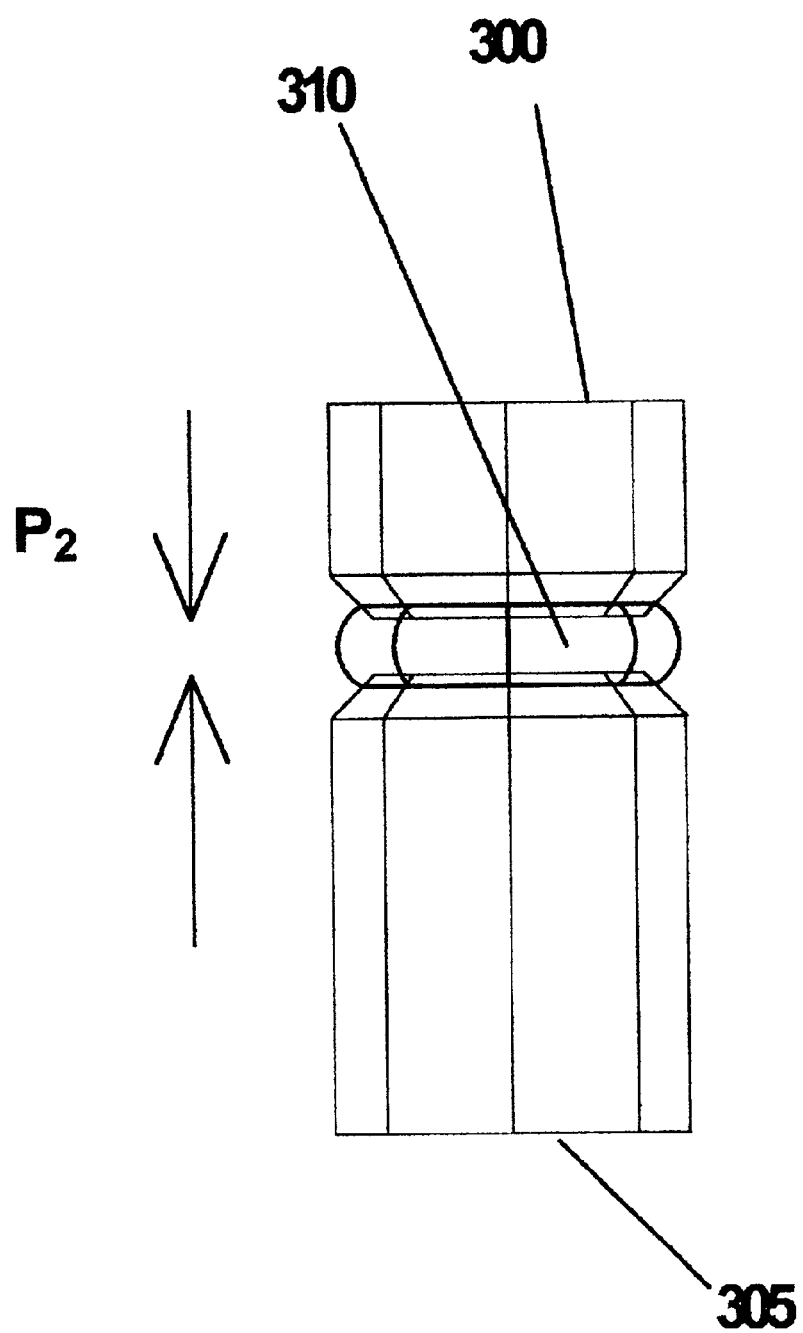

Samples can also be measured with a differential absorbance path as shown in FIG. 8. Here sample absorbance can be measured by changing the optical path over which the absorbance is measured, measuring the sample at each of one or more path lengths, where the difference in path length combined with the difference in transmitted intensity can be used to calculate the sample absorbance. This can be of significant value where the sample is strongly absorbing and the difference in path length can be determined more accurately than the absolute path length of the apparatus in the measurement position. Measurements are taken as shown in FIG. 8, where sample 9 is shown with a relatively long path $P_1$ and with a relatively short path length $P_2$ between the moveable anvils with one or more path differences $\Delta P$ with the absorbance at the shorter path $P_2$ being subtracted from the absorbance of one or more of the longer paths to arrive at the absorbance of the sample.

Figure 9:
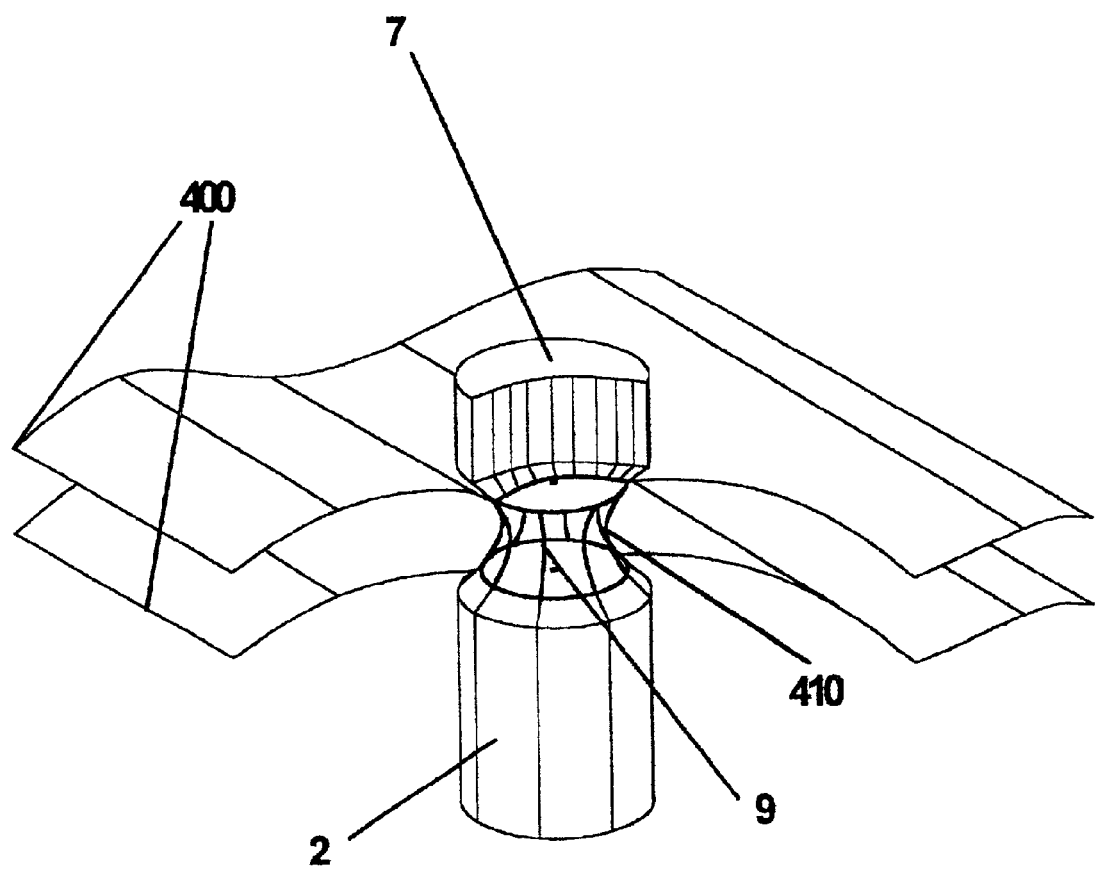
FIG. 9 shows a perspective view of a measurement made in the instrument of the invention holding the sample between two transparent sheets.
Figure 10:
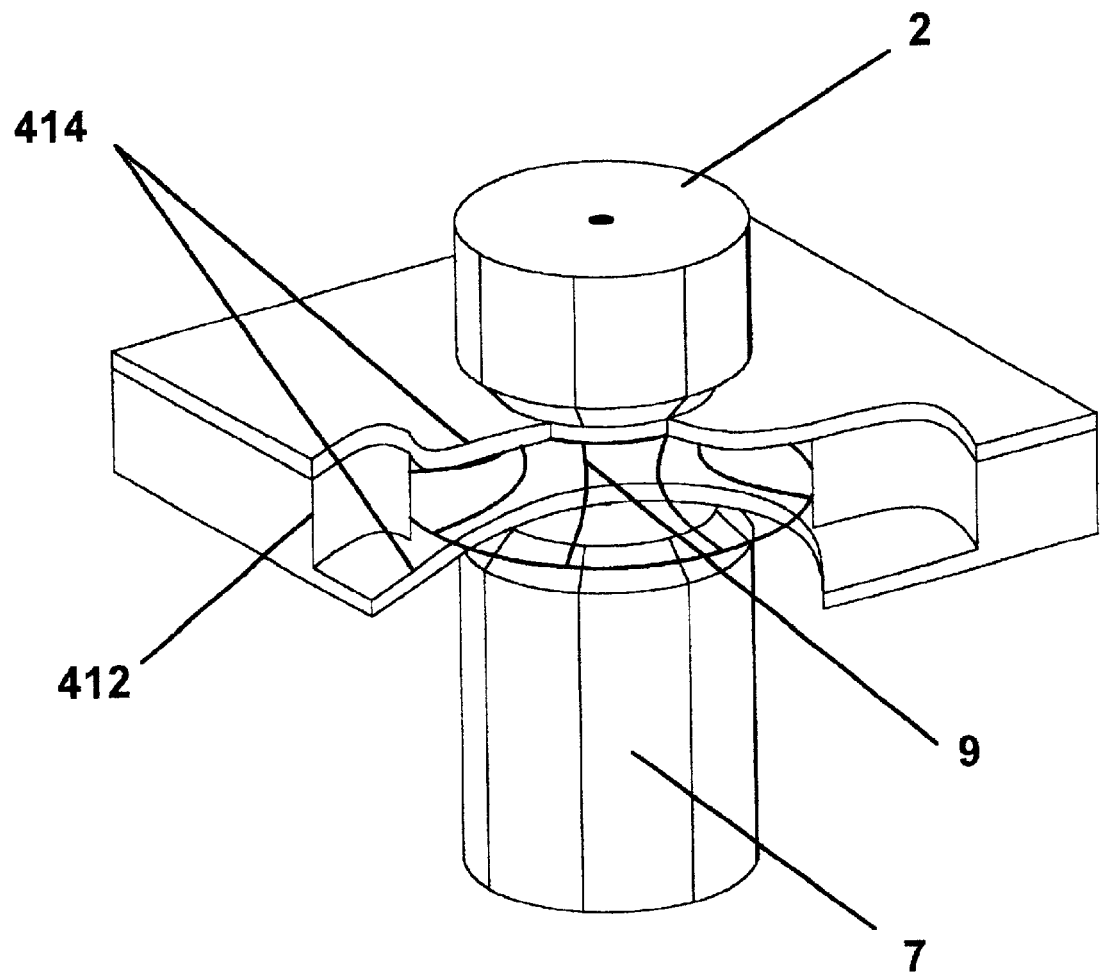
FIG. 10 shows a perspective view of a measurement made in the instrument of the invention holding the sample within a transparent container with flexible walls.

Samples can also be contained between two thin sheets of optically transparent material like Teflon™ or polyethylene films. As shown in FIG. 9, the same sort of column drawn between the two parts of the sample apparatus can be drawn between the two thin optical sheets 400 where the anvils of the apparatus are wetted to the film surfaces to minimize reflection at the interface and aid in pulling the measurement column. This would be of significant use where samples are corrosive or dangerous to handle for safety reasons and containment of the sample is preferred. The two containing sheets 400 allow the two anvil surfaces 2 and 7 of the sample apparatus to draw the sample 9 into column 410. Differential measurement of the sort discussed above in conjunction with FIG. 8 would be of significant value in this sort of measurement as the effects of the interfaces could be minimized with differential measurement. The two sheets 400 can be replaced by a small vessel 412, see FIG. 10, with flexible walls 414 such that the sample contained can be pulled into a measurement column. The column is pulled by pushing the anvils of the apparatus into the film of walls 414 until contact with the sample is made by both films, then drawing the measurement column. If separation of the anvils in the measurement position is less than the separation of the outside surfaces of the containing walls 414, the compliance of the walls will cause them to remain in contact with the anvils. Wetting the anvils before making contact will assist in maintaining contact and in minimizing reflection at the interface between the film and the optical fiber imbedded in the anvil. Once the measurement column is pulled, absorbance can be measured as a difference in absorbance between two path lengths.

What is claimed is:

1. A photometric or spectrophotometric apparatus wherein a sample in the form of a liquid drop is contained in tension by surface tension forces between two surfaces, one containing a photometric or spectrophotometric source and the other a photometric or spectrophotometric detector and an optical path is established through the sample between the two surfaces, said apparatus comprising:

first and second anvil surfaces at least one being moveable relative the other to any one of three positions;

an adjustable sample loading position so selected that the at least one moveable surface and the other surface are so remotely spaced that a liquid sample can be placed on the first surface;

an adjustable sample compression position so selected that the surfaces are opposed and substantially parallel and proximally spaced so that the liquid wets and spreads upon both surfaces; and an adjustable sample measuring position so selected that the opposed substantially parallel surfaces are spaced apart to pull the sample into a column wherein it is contained in tension by surface tension thereby providing an optical path for a photometric or spectrophotometric measurement; the improvement comprising:

providing means for limiting the surface area of the drawn column on at least one surface.

2. The apparatus of claim 1 wherein the surface area is limited by providing the surface area with a sharp edge.

3. The apparatus of claim 1 wherein the anvils are of unequal size.

4. The apparatus of claim 1 wherein the surface area is limited by providing the surface area with a change in surface tension characteristics.

5. The apparatus of claim 4 wherein the surface area is delimited by a low-surface-tension polymeric material forming a boundary.

6. The apparatus of claim 4 wherein the delimitation is bound on the inside.

7. The apparatus of claim 4 wherein the delimitation is bound on the outside.

* * * * *